United States Patent [19]
Barasz

[11] Patent Number: 4,721,465
[45] Date of Patent: Jan. 26, 1988

[54] DENTAL DAM WITH INTEGRAL DEFORMABLE FRAME

[76] Inventor: Steven G. Barasz, 83 Surrey La., Guilford, Conn. 06437

[21] Appl. No.: 26,853

[22] Filed: Mar. 17, 1987

[51] Int. Cl.⁴ ............................................... A61C 5/14
[52] U.S. Cl. .................................................... 433/137
[58] Field of Search ............................... 433/136, 137

[56] References Cited

U.S. PATENT DOCUMENTS 3,781,994  1/1974  Hesselgrew ......................... 433/137
4,664,628  5/1987  Totaro ................................... 433/136

Primary Examiner—Robert Peshock
Attorney, Agent, or Firm—William W. Jones

[57] ABSTRACT

The dental dam has a thin elastomeric web portion which overlies a portion of the patient's face and which may be punctured to allow one or more teeth to protrude through the web. The dam also includes a plastic frame which is integral with the web at the periphery of the web. The frame can be bent to conform to the shape of the patient's face and will retain its bent configuration during subsequent use of the dam. After the dental procedure involving the dam is completed, the dam, web and frame, are discarded.

13 Claims, 6 Drawing Figures

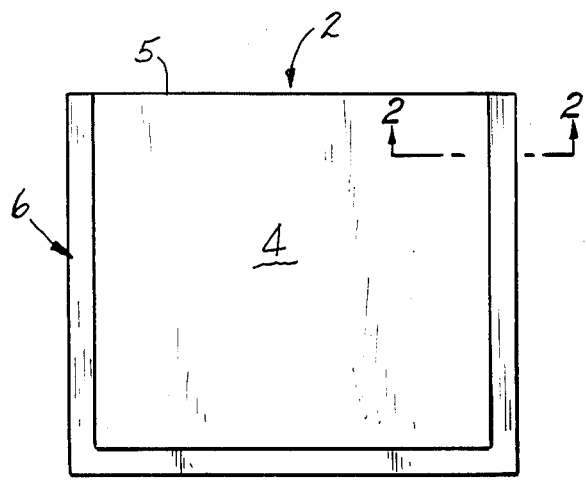
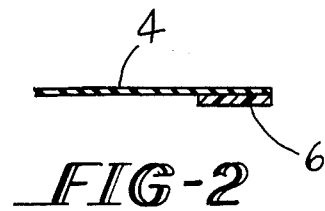
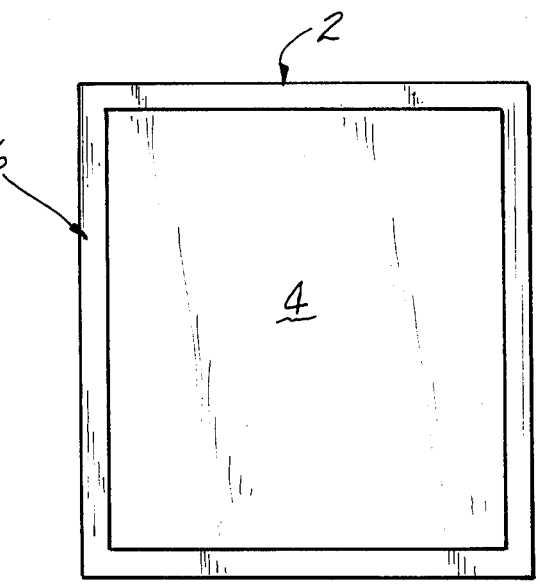
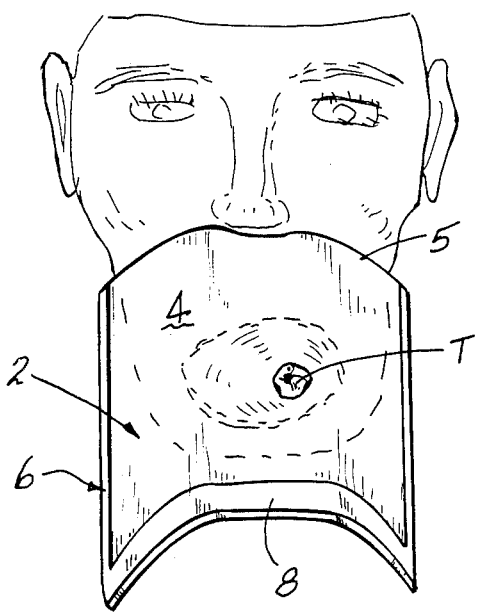
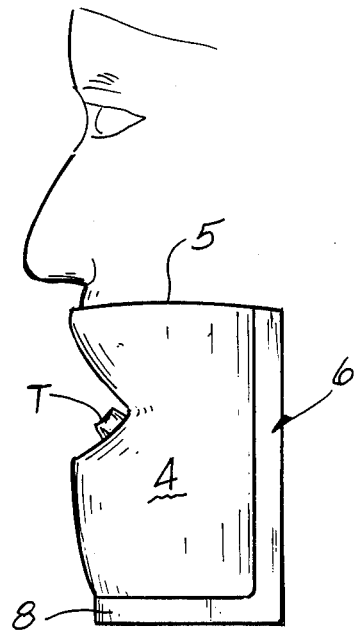
FIG-1
FIG-2
FIG-5
FIG-6
FIG-3
FIG-4

DENTAL DAM WITH INTEGRAL DEFORMABLE FRAME

This invention relates to an improved dental dam which is disposable after one use and which includes a web portion and a frame portion for the web, both of which portions are permanently joined together to form the dam. More particularly, this invention relates to a one piece all plastic dental dam having a web and an integral frame, the latter of which is deformable to fit the particular contours of a patient's face and which will remain in its contoured shape while the dental procedures are being performed.

The use of elastomeric sheetlike dental dams to isolate one or more teeth during dental procedures is commonplace. The dam will include a thin web of elastomeric material, such as latex or the like, which will either have preformed openings, or can be cut to form openings, which openings will be fitted about the tooth or teeth to be worked on. The rest of the web then preferably covers the mouth, tongue and lips so that the isolated tooth (or teeth) will remain dry during the dental procedure. Auxiliary metal or plastic clamps are generally used to ensure that the tooth and web stay properly arranged during the ongoing dental procedure. Alternatively, the prior art suggests the use of integral ridges on the web around the openings for the tooth, which ridges will grip the sides of the tooth or teeth when the latter are disposed in the openings, in order to dispense with the need for clamps on the teeth.

Conventionally, a frame will also be used to hold the periphery of the web in place around the patient's face to ensure that the entire mouth stays covered. The frame will typically be a separate member which is secured to the periphery of the web by the use of barbs, or the like, on the frame which pierce the web. The frame can be metal, or can be plastic to allow X-rays to be taken while the dam is on the patient. The frame will also typically be preformed, so as to be contoured to the patient's face so as to generally follow the lines of the patient's jaw.

U.S. Pat. No. 3,781,994 to Hesselgren discloses a dental dam with an integral frame which is inflatable to stretch the sheet part of the dam over the patient's mouth. Other U.S. Patents which disclose dental dams are: U.S. Pat. Nos. 741,890 Craigie; 1,292,133 Stoughton; 2,092,549 Craigie; 4,240,789 Rosenthaler; 4,512,742 Shanel; 4,583,946 Shanel; and 4,600,387 Ross.

The use of a separate frame and web to form the dental dam is undesirable. The sheet itself is, of course, discarded after use, but the frame is reused. This reuse of the frame requires that the frame be sterilized after each use and maintained in a sterile state until the next use. The dentist also must have available a number of different sized frames because of different sized patients. For example, a frame sized to fit an adult male may not be suitable for use on a female or on a child patient, and vice versa.

The dental dam of this invention is a completely disposable sterile article which has a thin web portion of latex or the like, and which also has a frame connected to the periphery of the sheet or web portion. The frame is permanently bonded to the periphery of the web, and is made from a bendable plastic material which will retain the configuration into which it is bent. A suitable plastic from which the frame can be made is polysulfone. Polysulfone possesses suitable rigidity to serve as a frame for stretching the web over the patient's face, and yet is sufficiently malleable to be easily bent to conform to the size and shape of the patient's face, particularly the cheeks and jaw. The two components, ie the web and rame, will be separately formed, enmass, and then assembled. The frames can be joined to the webs by a heat bond, by an adhesive, or by sonic welding, or the like. The dams will preferably be packaged in a flat configuration, in individual sterile packages. When one of the dams is used, the frame will be bent around the face of the patient so that the dam conforms to the individual shape of the patient's face, and yet stretches the web portion in a suitable fashion. The openings for the teeth will preferably be formed by the dentist piercing the web, and clamps, or the like, may be used to gird the teeth isolated by the dam.

It is therefore an object of this invention to provide an improved disposable dental dam having a thin web portion for covering the mouth to isolate one or more teeth, and having a frame permanently joined to the web for stretching the web over the patient's face.

It is a further object of this invention to provide a dental dam of the character described wherein the frame may be bent from a flat configuration to a bent configuration to conform to the general shape of a patient's face.

It is an additional object of this invention to provide a dental dam of the character described wherein the frame will retain the bent configuration to stretch the web over the patient's mouth.

It is another object of this invention to provide a dental dam of the character described which can be packaged in individual sterile packages.

These and other objects and advantages of this invention will become more readily apparent from the following detailed description of preferred embodiments of the invention when taken in conjunction with the accompanying drawings, in which:

FIG. 1 is a plan view of a first embodiment of a dental dam formed in accordance with this invention;

FIG. 2 is a fragmented sectional view of the dam taken along line 2—2 of FIG. 1;

FIG. 3 is a perspective view of the dam of FIG. 1 fitted onto a patient;

FIG. 4 is a side view of the patient with the dam in place;

FIG. 5 is a fragmented side elevational view showing how a tooth is isolated from the rest of the mouth with the dam; and FIG. 6 is a plan view of a second embodiment of a dam formed in accordance with this invention.

Referring now to the drawings, there is shown in FIG. 1 a preferred embodiment of a dental dam, denoted generally by the numeral 2, formed in accordance with this invention. The dam 2 includes a central thin sheet or web portion 4 and a U-shaped frame portion 6. It will be noted that the top edge 5 of the web 4, as viewed in FIG. 1, is not bordered by the frame 6. The web 4 is preferably formed from an elastomeric material such as latex rubber, and the frame 6 is formed from a plastic material which can be manually bent into different shapes, and, once bent, will remain in the shape imparted to it, unless intentionally reformed, One such plastic material preferred for use as the frame is polysulfone. The web 4 and frame 6 are formed separately, but are joined together by a permanent bond, as with a suitable adhesive, or by means of a heat melt bond, or by sonic welding. As noted in FIG. 2, the frame 6 has a thin rectangular cross-sectional shape, and the web 4 is bonded to one side of the frame 6. The frame 6 will preferably be molded in one piece, and subsequently bonded to the web 4. The dam is preferably a square, with five or six inch sides, for example.

Referring to FIGS. 3 and 4, the manner in which the dam 2 is custom fitted onto a patient is shown. The top edge 5 of the dam 2 is placed beneath the patient's nose, and the lower leg 8 of the frame 6 is bent by the dentist around the patient's jaw. The tooth T which is to be isolated is identified and a hole is formed in the web 4 over the tooth T. The dentist then pushes the tooth T through the hole, and a clamp 10 may be used to hold the web 4 down around the base of the tooth T, as shown in FIG. 5.

FIG. 6 shows a second embodiment of the dam 2 wherein the web 4 is bounded on all four sides by the frame 6. The basic mode of operation of the embodiment shown in FIG. 6 is the same as set forth above.

It will be readily appreciated that the dental dam of this invention will be discardable after one use, can be manufactured, sold and stored in a flat configuration, and can be custom conformed to each patient's face for use. The dam, being entirely plastic, can be worn during X-rays with no problems. The dams can be individually packaged in sterile packages thereby eliminating the need to sterilize the components in the dentist's office. The dams are inexpensive to produce, convenient to use, and sanitary.

Having described preferred embodiments of the invention, it is not intended to limit the invention otherwise than as required by the appended claims.

What is claimed is:

1. A one piece dental dam designed to be discarded after a single use, said dam comprising:
   a. a thin elastomeric web adapted to be placed over a patient's face to cover the patient's mouth during a dental procedure and selectively rupturable to form an opening to allow one or more teeth to be exposed; and
   b. a frame permanently bonded to said web, said frame forming a border for said dam at a periphery of said web, said frame being manually deformable to conform generally to the contours of a patient's jaw and cheeks whereby the dam can be packaged in a flat form and then custom fitted onto a patient's face during use, the frame being operable to stretch the web over the patient's face.

2. The dental dam of claim 1 wherein said frame is formed from a polymeric material which is substantially transparent to X-rays.

3. The dental dam of claim 2 wherein said frame is formed from polysulfone.

4. The dental dam of claim 2 wherein said frame is bonded to said web by sonic welding.

5. A disposable dental dam comprising:
   a. a thin elastomeric web having a substantially rectangular configuration, said web being adapted to cover a patient's mouth and being rupturable in order to isolate one or more teeth during a dental procedure; and
   b. a polymeric frame bonded to edge portions of said web, said frame being manually deformable to conform generally to the contour of a patient's jaw and cheeks whereby the dam can be packaged in a flat form and then cutom fitted onto a patient's face during use, the frame being operable to stretch the web over the patient's face.

6. The dental dam of claim 5 wherein said frame is U-shaped and bonded to three edges of said web.

7. The dental dam of claim 5 wherein said frame is rectangular and is bonded to each edge of said web.

8. The dental dam of claim 5 wherein said frame is made from polysulfone.

9. The dental dam of claim 5 wherein said frame is bonded to said web by sonic welding.

10. A disposable dental dam comprising:
    a. a thin latex web having a substantially rectangular configuration, said web being operable to cover a patient's mouth and being rupturable in order to isolate one or more teeth during a dental procedure; and
    b. a polysulfone frame bonded to edge portions of said web, said frame being manually deformable to conform generally to the contours of a patient's face whereby the dam can be packaged in a flat form and then custom fitted onto a patient's face during use, the frame being operable to stretch the web over the patient's face.

11. The dental dam of claim 10 wherein said frame is U-shaped and is bonded to three edge portions of said web.

12. The dental dam of claim 10 wherein said frame is rectangular and is bonded to each edge of said web.

13. The dental dam, of claim 10 wherein said web is sonic welded to said frame.

* * * * *